(12) United States Patent
Wey

(10) Patent No.: US 6,516,229 B1
(45) Date of Patent: *Feb. 4, 2003

(54) PERSONAL THERAPEUTIC DEVICE USING FAR INFRARED RADIATION

(76) Inventor: Albert Chin-Tang Wey, 233 E. 57th St., Westmont, IL (US) 60559

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/449,241
(22) Filed: Nov. 24, 1999
(51) Int. Cl.[7] .................................................. A61F 2/00
(52) U.S. Cl. .......................................... 607/100; 607/96
(58) Field of Search ................................. 607/100, 111, 607/96; 250/504; 5/421

(56) References Cited

U.S. PATENT DOCUMENTS

| | | | |
|---|---|---|---|
| 4,680,822 A | * 7/1987 | Fujino et al. | 5/421 |
| 4,886,972 A | * 12/1989 | Nakai et al. | 250/504 |
| 4,976,706 A | 12/1990 | Aki | |
| 5,451,199 A | 9/1995 | Kim | |
| 5,894,067 A | 4/1999 | Kim | |
| 6,026,330 A | * 2/2000 | Chuang | 607/100 |
| 6,120,531 A | * 9/2000 | Zhou et al. | 607/111 |

\* cited by examiner

*Primary Examiner*—Michael Peffley
*Assistant Examiner*—Peter J Vrettakos
(74) *Attorney, Agent, or Firm*—Piper Rudnick

(57) ABSTRACT

This invention describes a personal therapeutic device comprising a supporting means with a far infrared ray emitting body placed thereon that provides a means for enhancing the health conditions of human beings. The device can be carried externally on the section of human body to be exposed to far infrared radiation. The result is improved blood circulation and metabolism and reduced stress and fatigue.

12 Claims, 1 Drawing Sheet

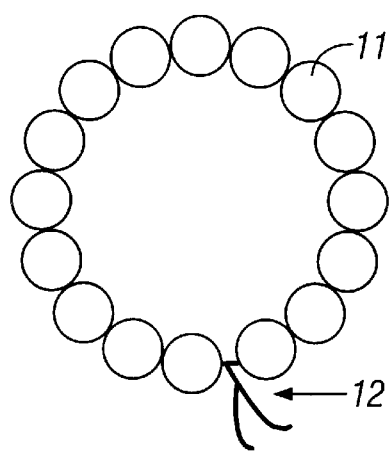
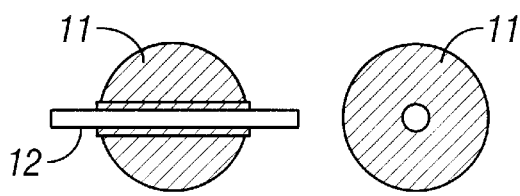
FIG. 1           FIG. 2
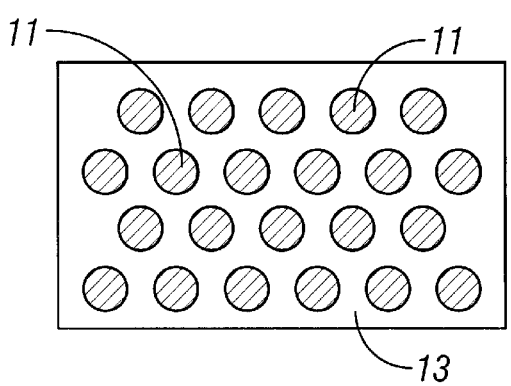
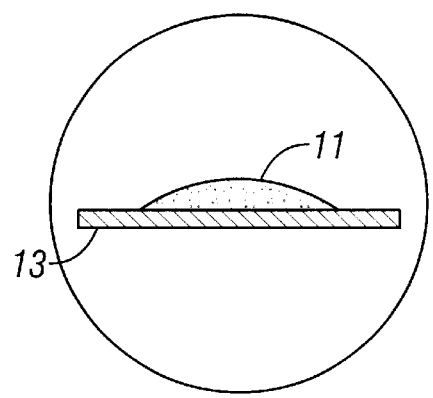
FIG. 3           FIG. 4
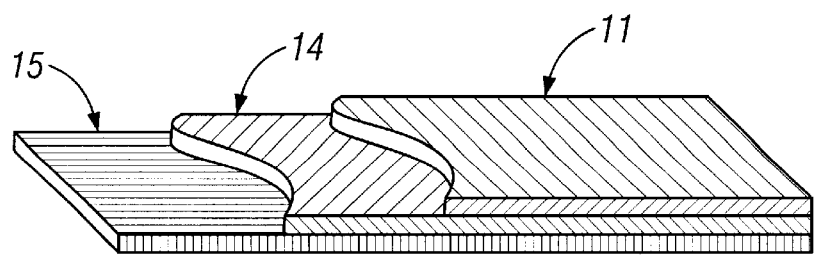
FIG. 5

PERSONAL THERAPEUTIC DEVICE USING FAR INFRARED RADIATION

BACKGROUND

1. Field of Invention

This invention relates to a therapeutic device comprising a far infrared ray emitting material that can be mounted adjacent to and exterior of a human body to enhance circulation and metabolism, as well as to recover from stress and fatigue, in order to maintain the health and coordination of the body.

2. Description of Prior Art

There have been several types of devices developed for improving and maintaining health of human body. For example, one type of devices included a magnetic radiating unit on a far infrared ray generating composition plate (U.S. Pat. No. 5,451,199 and 5,894,067), the other devices comprised both germanium powder and ceramic powder for skin contact medical treatment (U.S. Pat. No. 4,976,706). Not only these devices do not work satisfactorily, but also they require complicated mechanism to work with the mixed effects from magnetic field and far infrared radiation in the case of U.S. Pat. No. 5,451,199, or from activating germanium powder and far infrared radiating ceramic powder in the case of U.S. Pat. No. 4,976,706. Both cases might have recognized the potential of far infrared radiation in improving living body functions, but had improperly used it rather as an accessory, a heating source, than as a primary source for cure due to low radiation capacity of the far infrared ray emitting materials used.

Since the first discovery of the infrared ray by a German physicist, various attempts have been made to utilize the same by generating stable far infrared rays having a predetermined period, or wavelength. It has been realized that the far infrared radiation in the wavelength band between 2.5 $\mu$m (microns or micrometers) and 30 $\mu$m plays a key role in heating and drying.

It is further known that far infrared radiation in a wavelength band of 3.5 $\mu$m to 14 $\mu$m has a strong resonance effect to substance in which hydrogen-bonding exists. According to Organic Chemistry there exists dipole-dipole interaction between polarized molecules. Hydrogen-bonding is an example of strong dipole-dipole interaction. The electric potentials of such dipole-dipole interactions are in the range of 0.04 eV to 0.5 eV. Based on a simplified equation that governs the relationship between electric potential (eV) and the photon energy E associated with a wavelength $\lambda(\mu m): \lambda (\mu m) = 1.2398 \ (eV-\mu m)/E(eV)$, such dipole-dipole interactions will resonate with the electromagnetic waves having wavelengths between 2.5 $\mu$m to 30 $\mu$m, which fall in the far infrared radiation zone.

For example, the water molecules are polarized in nature. It means that the hydrogen atoms and oxygen atoms in water molecules are charged and tend to create a static hydrogen-bonding between water molecules. As a result, the charged water molecules gather and form a large cluster. The hydrogen-bonding between water molecules can be resonantly broken by a far infrared radiation at about 3.5 $\mu$m wavelength into individual molecules or molecule clusters of smaller sizes with better mobility and penetration. In addition, a 6.27 $\mu$m far infrared radiation can further activate the water molecules, transferring photon energy of the radiation into symmetrically rotational movement of the atoms in the water molecules.

Numerous clinical studies have manifested various effects of far infrared radiation on human bodies such as rise in subcutaneous temperature, enhancement of blood circulation and metabolism, mitigation of sensitive nerves, and so on. Studies also demonstrated that exposure to far infrared radiation could activate the strained molecules in stressed muscles and help recovering from fatigue.

The far infrared ray emitting body is typically composed of oxides selected from the group consisting alumina, silica, alumina hydrate, silica hydrate, zirconia, lithium oxide, magnesium oxide, calcium oxide, titanium oxide, or a mixture of said oxides. Nevertheless, a far infrared rays emitting material with strong radiation capacity is needed in order to permeate into 10 to 40 mm below the skin of a human body to activate cells.

The present inventor has undertaken extensive studies to select a far infrared ray generating composition that possesses a strong radiation capacity in the desirable band of wavelengths, namely 3.5 to 14 $\mu$m. As a result, the inventor found that the far infrared ray generating composition fabricated by the method involving inorganic powders having particle sizes smaller than 3,000 angstroms provided a larger radiation effect that could be attributed to larger specific radiation surface areas. A sample composition and fabrication method can be found in, for example, U.S. Pat. No. 4,886,972. The inventor further found that only those far infrared emitting body comprising mixtures of compounds having an ultrafine inorganic powder with a particle size smaller than 1,000 angstroms, preferably below 200 angstroms, would emit considerable radiation that could effectively activate the cells in human body at a very significant level.

Objects and Advantages

Accordingly, one object of this invention is to provide a personal therapeutic device that can activate the human body to enhance circulation and metabolism, as well as to recover from stress and fatigue. As a result, this device can maintain the health and coordination and enhance living functions of the human body.

Another object of the present invention is to provide an easy-to-wear or —carry and yet effective human body condition enhancement device.

These objectives are achieved by a device comprising:

a supporting means; and a far infrared ray emitting body disposed on said supporting means.

Other objects, features and advantages of the present invention will hereinafter become apparent to those skilled in the art from the following description.

DRAWING FIGURES

FIG. 1 shows a schematic plan view illustrating one embodiment of the present invention with a far infrared ray emitting body in a form of beaded bracelet or necklace.

FIG. 2 is a schematic enlarged cross section of the bead in FIG. 1.

FIG. 3 shows a schematic plan view illustrating another embodiment of the present invention with plural far infrared ray emitting elements printed on a sheet.

FIG. 4 is a schematic enlarged cross section of the far infrared ray emitting element on the fabric sheet as shown in FIG. 3.

FIG. 5 shows a cutaway perspective view of another embodiment of the present invention with the far infrared ray emitting material uniformly disposed on a pliable sheet with an adhesive layer.

Reference Numerals in Drawings

| 11 Far infrared ray emitting material | 12 Elastic string |
| --- | --- |
| 13 Fabric sheet | 14 Pliable laminate substrate |
| 15 Adhesive layer | |

SUMMARY

In accordance with the present invention a personal therapeutic device comprises a supporting means and a far infrared ray emitting body. The device can be mounted, carried, or worn at close to where the artery passes for enhancement of circulation and metabolism, or at a selected place on the body for local treatment of fatigue and stress or for other therapeutic purposes.

DETAILED DESCRIPTION OF THE INVENTION

The device of the present invention comprises a supporting means that holds a far infrared ray emitting body 11. FIG. 1 shows a schematic plan view illustrating one embodiment of the present invention with a far infrared ray emitting body in a form of beaded bracelet or necklace. For example, a far infrared ray emitting bead 11 may have a typical diameter of about 3/8 to 1/2 inch (9.5 to 12.7 mm) with a 3/32 inch (2.4 mm) mounting hole through it. Typically, a bracelet may comprise 16 to 24 such beads depending on the wearer's wrist sizes. More beads but smaller in size are required for necklace, taking into consideration of the total weight of beads. FIG. 2 is a schematic enlarged cross section of the far infrared ray emitting bead 11 and an elastic string 12 that ties all beads together as shown in FIG. 1.

FIG. 3 shows a schematic plan view illustrating another embodiment of the present invention with plural far infrared ray emitting elements 11 printed on a sheet 13. This arrangement constitutes a basic element of far infrared ray emitting sheet material that can be used to construct cloths, hair caps, eye masks, head bands, wrist bands, waist bands, and the like. The sheet material 13 may be woven fabrics, various synthetic resin films, or the like, preferably those having gas permeability. The coating of far infrared emitting material 11 on the sheet 13 can be carried out by printing the selected infrared ray emitting ceramic powders with an adhesive such as polyvinyl alcohol, silicone resin, or the like, on the surface of the sheet 13. The ceramic powders can be printed as a round spot at a diameter of 3/64 inch (1. 5 mm) each and 3/64 inch (1.5 mm) apart to fill the surface area of the sheet. FIG. 4 shows a schematic enlarged cross section of the printed ceramic element 11 on the sheet 13 as shown in FIG. 3.

FIG. 5 shows a cutaway perspective view of another embodiment of the present invention with a far infrared ray emitting material 11 disposed on a pliable sheet 14 with an self-adhesive layer 15. The ceramic powder can be uniformly coated on or impregnated in a pliable sheet by deposition, sputtering or other known techniques. The pliable sheet again can be woven fabrics, resin coated cloth, various synthetic resin films, or the like, that can be attached to a self-adhesive layer. This self-adhesive far infrared radiating device can be placed on, for example, cell phone, cordless phone, or electric shaver to eliminate or minimize the adverse effect caused by the electromagnetic fields radiated from the electronic devices.

Example

A qualitative and comparative method was employed to measure the far infrared radiation strengths during selecting ceramic compositions and particle sizes. A regular for-family-use liquidized natural gas burner was used as a measurement tool. It was known that far infrared radiation could penetrate rubber hose and activate the fuel passing through in the hose. The dipole-dipole interactions between hydrocarbon molecules resulting in the formation of large clusters can be overcome by a far infrared radiation in the same wavelength band as designed in the present invention. The far infrared radiated fuel led to a more complete combustion because of smaller fuel particles that were easier to mix with oxygen uniformly. It resulted in a stronger flame. Accordingly, the relative radiation strengths from various ceramic compositions with different particle sizes could be evaluated and determined qualitatively based on the quantified relative changes in the resultant flame's strength (or height). A commercially available ceramic composition made in Japan that had a particle size around 200 $\mu$m and a wavelength band between 4 $\mu$m to 14 $\mu$m was thus finally chosen and used to form a beaded bracelet. The diameter of the beads is approximately 3/8 inch (9.5 mm). A significant drop in blood pressure of a 58-year-old hypertension patient was observed after he had worn the bracelet for 30 minutes.

Conclusion, Ramifications, and Scope

According to the present invention, a personal therapeutic device comprising a supporting means and a far infrared ray emitting body having a particle size smaller than 3,000 angstrom, preferably 200 angstrom or smaller, can effectively activate the water molecules, cells and other chemistry in the human body. As a result, this device will enhance blood circulation and metabolism of human body and help recover from fatigue and stress. The device can be used to maintain the health and coordination of the human body or used for other therapeutic purposes.

The invention has been described above. Obviously, numerous modifications and variations of the present invention are possible in light of the above teachings. Such variations are not to be regarded as a departure from the spirit and scope of the invention and all such modifications as would be obvious to one skilled in the art are intended to be included within the scope of the following claims.

I claim:

1. A device mounted adjacent to and exterior of a human body for enhancement of health conditions, said device comprising:

a plurality of beads formed of a far infrared ray emitting material threaded on a support member, said far infrared ray emitting material being formed of far infrared ray emitting particles having an ultrafine particle size, and a radiation capacity in the band of wavelengths between 3 and 14 microns.

2. The device according to claim 1 wherein the particles are selected from the group consisting of alumina, silica, alumina hydrate, silica hydrate, zirconia, lithium oxide, magnesium oxide, calcium oxide, titanium oxide, or a mixture of said oxides.

3. The device according to claim 1, wherein said ultrafine powder has a particle size 1,000 angstroms or below.

4. The device according to claim 1 wherein said support member is a string.

5. A device according to claim 1 wherein said particle size is 200 angstroms or less.

6. A method for irradiating a portion of a human body, comprising:

providing a plurality of beads formed of a far infrared ray emitting material, said far infrared ray emitting material being formed of far infrared ray emitting particles having an ultrafine particle size, and a radiation capacity in the band of wavelengths between 3 and 14 microns;

threading said plurality of beads on a support member; and mounting said threaded beads around a portion of a human body.

7. The method according to claim 6, wherein sources of magnetic influence are cleared from a region adjacent the human body.

8. A method for irradiating a portion of a human body, comprising:

providing a sheet-like carrier;

printing a matrix of a far infrared ray emitting material on a surface of the sheet-like carrier, said far infrared ray emitting material being formed of far infrared ray emitting particles having an ultrafine particle size, and a radiation capacity in the band of wavelengths between 3 and 14 microns; and mounting said carrier around a portion of a human body.

9. The method according to claim 8 wherein said carrier comprises a cloth material.

10. The method according to claim 8 wherein said carrier comprises a rubber material.

11. The method according to claim 8 wherein said carrier comprises a resin material.

12. A method for irradiating a portion of a human body, comprising:

providing a sheet-like carrier;

coating or impregnating the sheet-like carrier with far infrared ray emitting material, said far infrared ray emitting material being formed of far infrared ray emitting particles having an ultrafine particle size, and a radiation capacity in the band of wavelengths between 3 and 14 microns; and mounting said carrier around a portion of a human body.

* * * * *